United States Patent [19]

Schaus

[11] Patent Number: 4,939,259
[45] Date of Patent: Jul. 3, 1990

[54] 2-OXO-PYRIDO[2,3-G]QUINOLINE DERIVATIVES

[75] Inventor: John M. Schaus, Indianapolis, Ind.

[73] Assignee: Eli Lilly and Company, Indianapolis, Ind.

[21] Appl. No.: 383,673

[22] Filed: Jul. 24, 1989

[51] Int. Cl.⁵ ............................................. C07D 471/04
[52] U.S. Cl. ......................................................... 546/81
[58] Field of Search ................ 540/470, 481, 575, 597; 544/126, 361; 546/81; 514/183, 210, 212, 218, 232.8, 254, 292

[56] References Cited

U.S. PATENT DOCUMENTS

| | | | |
|---|---|---|---|
| 3,790,577 | 2/1974 | Waring | 546/81 |
| 4,198,415 | 4/1980 | Kornfeld et al. | 546/82 |
| 4,235,909 | 11/1980 | Bach et al. | 424/258 |
| 4,501,890 | 2/1985 | Nichols et al. | 514/267 |
| 4,537,893 | 8/1985 | Titus et al. | 514/293 |
| 4,659,832 | 4/1987 | Schaus et al. | 546/83 |

FOREIGN PATENT DOCUMENTS 250179  6/1987  European Pat. Off. .

OTHER PUBLICATIONS

Bach et al., *J. Med. Chem.*, 23, 481, (1980).
Nordman et al., *J. Med. Chem.*, 28(3), 367 (1985).

*Primary Examiner*—Robert W. Ramsuer
*Attorney, Agent, or Firm*—Douglas J. Taylor; Leroy Whitaker

[57] ABSTRACT

Trans-(±)-2-(substituted)-6-(substituted)-5,5a,6,7,8,9-,9a,10-octahydrophrido[2,3-g]quinolines are useful in treating a variety of disorders including Parkinsonism, anxiety, depression, hypertension, glaucoma, sexual dysfunction, and prolactin mediated disorders such as galactorrhea, amenorrhea, prolactinoma and the inhibition of postpartum lactation.

1 Claim, No Drawings

2-OXO-PYRIDO[2,3-G]QUINOLINE DERIVATIVES

BACKGROUND OF THE INVENTION

The ergoline ring is a tetracycle having the following structure

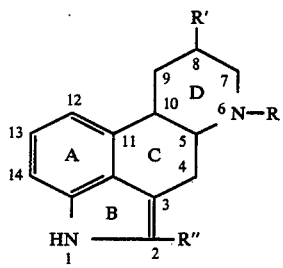

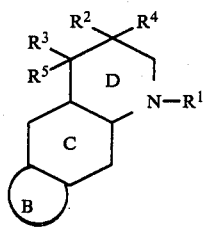

wherein the C- and D-rings are trans-fused and wherein the B-ring may be either a pyrimidine, thiazole, pyrazole, oxazole or pyrrole ring are disclosed in European Patent Application No. 250,179. These compounds are also D-2 dopamine agonists, and are prepared as racemates.

Certain substituted ergolines are known to be D-2 dopamine agonists having the ability to inhibit the secretion of prolactin and to affect favorably the symptoms of Parkinson's Syndrome. For example, in the foregoing structure when R is n-propyl, $R^1$ is methylthiomethyl, and $R^2$ is H, the substituted ergoline has been given the generic name pergolide, which is disclosed in U.S. Pat. No. 4,166,182. Pergolide has been proven to be effective in the treatment of some symptoms of Parkinsonism, and is being developed as the mesylate salt. Another such ergoline drug is α-bromoergocryptine, named generically as bromocryptine. It is disclosed in U.S. Pat. Nos. 3,752,814 and 3,752,888. For bromocryptine, $R^2$ is Br, R is methyl and R' is the ergocryptine side chain. While both ergolines are D-2 dopamine agonists, bromocryptine, and to a lesser extent pergolide, also have some α-blocking activity.

BCD tricyclic ergoline part-structure compounds having the following formula

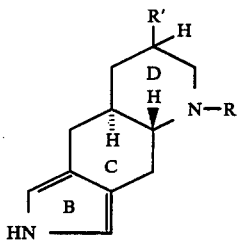

wherein R is lower alkyl, have been synthesized, and are disclosed in Bach et al., *J. Med. Chem*, 23, 481 (1980) and U.S. Pat. No. 4,235,909. These products were prepared as racemates composed of the enantiomer illustrated above together with the mirror image thereof. In both enantiomers the R' substituent is equatorial. These compounds show activity in prolactin inhibition and rat-turning behavior tests, indicating that D-2 dopamine agonist activity is present. Related compounds in which the C-1 carbon is replaced by nitrogen to form a pyrazole ring are also disclosed by Bach et al. in *J. Med. Chem.*, 23, 481 (1980) and in U.S. Pat. No. 4,198,415. These pyrazoloquinolines are also D-2 dopamine agonists, and they too were prepared only as the racemate wherein the R' substituent of each enantiomer is equatorial.

Other BCD tricyclic ergoline part-structure compounds having the following general formula

SUMMARY OF THE INVENTION

This invention provides new octahydropyrido[2,3-g]quinolines having various substituents at the 2- and 6-positions of the compounds. The compounds of the invention are useful for the treatment of a variety of disorders including Parkinsonism, depression, hypertension, anxiety, glaucoma, sexual dysfunction and prolactin mediated disorders such as galactorrhea, amenorrhea, prolactinoma and the inhibition of post-partum lactation.

DETAILED DESCRIPTION AND PREFERRED EMBODIMENTS

The present invention provides compounds of Formulae I

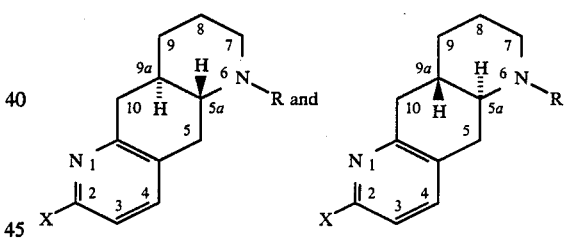

wherein:

X is halo, hydroxy, hydrogen, $C_1$–$C_4$ alkyl or a group of the formula —$NR^1R^2$, wherein $R^1$ and $R^2$ are individually hydrogen, $C_1$–$C_6$ alkyl, $C_2$–$C_6$ acyl, or $C_1$–$C_6$ alkylphenyl, or where $R^1$ and $R^2$, taken together with the nitrogen atom to which they are attached, form a three- to eight-membered heterocyclic ring containing either one or two nitrogen atoms, or one nitrogen atom and one oxygen atom;

R is $C_1$–$C_4$ alkyl, allyl, or cyclopropylmethyl; and pharmaceutically-acceptable salts thereof.

The invention also provides pharmaceutical formulations comprising a compound of Formulae I and a pharmaceutically acceptable carrier, diluent or excipient therefor. Further, embodiments of the invention include methods for treating a variety of disorders including Parkinsonism, depression, hypertension, anxiety, glaucoma, sexual dysfunction and prolactin mediated disorders such as galactorrhea, amenorrhea, prolactinoma and the inhibition of postpartum lactation. A final embodiment of the present invention are compounds of Formulae II

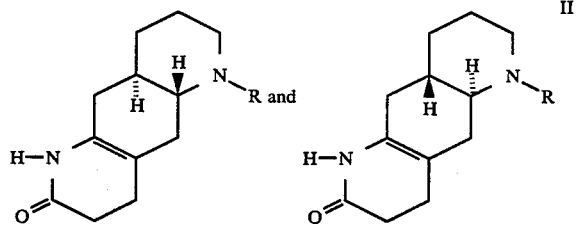

wherein R is as defined above, and acid addition salts thereof.

In the above formulae, reference to halo includes fluoro, chloro, bromo or iodo.

The term "$C_1$–$C_6$ alkyl" denotes radicals such as methyl, ethyl, n-propyl, iso-propyl, n-butyl, sec-butyl, tert-butyl, n-pentyl, n-hexyl, cyclopropyl, cyclobutyl, cyclopentyl, or other straight, branched or cyclic alkyls.

The term "$C_1$–$C_6$ alkylphenyl" denotes a straight or branched alkyl group substituted at any position by a phenyl ring. Examples of such a group include phenyl methyl (benzyl), 2-phenylethyl, 3-phenyl-(n-propyl), 4-phenylhexyl, 3-phenyl-(n-amyl), 3-phenyl-(sec-butyl), and the like.

The term "three- to eight-membered heterocyclic ring" denotes optionally substituted three-membered, four-membered, five-membered, six-membered, seven-membered or eight-membered rings which contain at least one nitrogen atom. Said rings may contain one additional heteroatom such as oxygen or nitrogen, in particular nitrogen, and may be saturated or unsaturated. Five-membered and six-membered rings are preferred. The following ring systems are examples of the heterocyclic substituents denoted by the term "three- to eight-membered heterocyclic ring": morpholine, piperazine, piperidine, pyrrolidine, azetidine, aziridine, homopiperazine, and the like. When such rings are substituted they may be substituted with groups such as $C_1$–$C_4$ alkyl, hydroxy, keto, amino, $C_1$–$C_4$ alkylamino, ($C_1$–$C_4$ alkyl)$_2$amino, and the like.

The term "$C_1$–$C_4$ alkyl" denotes such straight or branched radicals as methyl, ethyl, n-propyl, isopropyl, n-butyl, sec-butyl or tert-butyl. The preferred $C_1$–$C_4$ alkyl group is n-propyl.

The term "$C_2$–$C_6$ acyl" denotes straight or branched chain radicals such as acetyl, propionyl, n-butyryl, and the like.

The pharmaceutically-acceptable salts of compounds of Formulae I include salts derived from inorganic acids such as hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, and aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1, 4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and other like salts.

For compounds listed above in which X is hydroxy, it should be understood that the compounds exist as a tautomeric mixture having the following structures

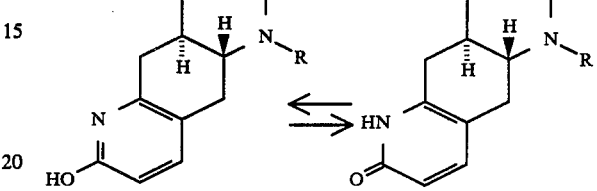

and

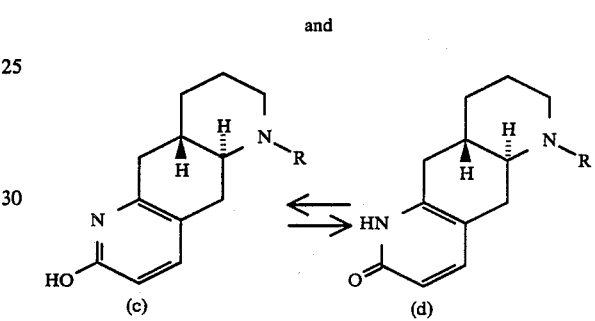

Tautomers (b) and (d) apparently predominate in the tautomeric mixture. However, the present invention encompasses each individual tautomer, as well as the tautomeric mixture, since an equilibrium mixture of the tautomers in always present.

As can be seen from Formulae I, the compounds of the present invention provide a racemic pair. Resolution of the racemic mixture into its optical enantiomers can be accomplished by procedures known to those skilled in the art. Accordingly, the individual enantiomers, as well as the racemic mixture itself, are all included within the scope of this invention.

While all of the compounds of the present invention are believed to be useful for treating the disorders noted above, certain of these compound are preferred for such uses. Preferred compounds of the present invention are those wherein R is $C_1$–$C_4$ alkyl or allyl. Especially preferred compounds are those wherein R is n-propyl. Preferred X substituents for the compounds of the invention are halo, especially chloro and bromo, hydrogen or a group of the formula —NR$^1$R$^2$, wherein R$^1$ and R$^2$ are as defined above. When R$^1$ and R$^2$, taken together with the nitrogen atom to which they are attached, form a three- to eight-membered heterocyclic ring, morpholino, piperazino, piperidino or pyrrolidino rings are preferred.

The synthesis of some of the compounds of Formulae I may be accomplished as depicted in the following schematic. In the following schematic, only one of the optical enantiomers is illustrated. However, one skilled in the art will readily appreciate that the synthetic scheme illustrated therein is readily applicable to the opposite optical enantiomer, as well as to the racemic mixture itself.

Scheme I

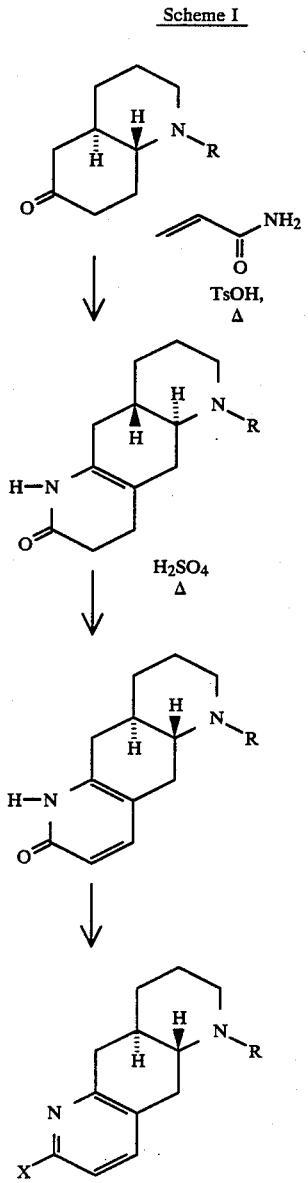

Compound A

Compound B

Compound C

Compound D

Compounds represented by Compound D in Scheme I are most easily prepared by utilizing a ketone starting material (Compound A) wherein R is $C_1$–$C_4$ alkyl, allyl or cyclopropylmethyl. The ketones represented by Compound A are preferably prepared as taught by Schaus, U.S. Pat. No. 4,540,787, issued Sept. 10, 1985, incorporated herein by reference. The ketone (either resolved or racemic) can then be reacted with acrylamide, p-toluenesulfonic acid monohydrate, and p-methoxyphenol in an inert solvent, with heat, to form Compound B, wherein R is as set forth above.

Compound B is next dehydrogenated using concentrated sulfuric acid and heat. The resultant Compound C, a trans-2-oxo-6-(substituted)-1,2,5,5a,6,7,8,9,9a,10-decahydropyrido[2,3-g]quinoline, is used as the basic intermediate for the synthesis of Compound D variants, wherein X is a taught for Formulae I above.

Compounds of Formulae I in which X is halo are prepared by reacting Compounds C with a dehydrating halogenating agent such as phosphorous oxychloride, phosphorous pentachloride, phosphorous tribromide, phosphorous triiodide, sulfur tetrafluoride, diethylaminosulfur trifluoride, or the like, to yield the corresponding halogenated analogue of Compound D. Said halogenated compounds serve as intermediates in the synthesis of other Compounds D, as well as being active compounds in and of themselves.

For example, nucleophilic displacement of the halogen atom by an amine provides Compounds D in which X is an amino substituent. Examples of such nucleophilic displacement reactions may be found in Examples 6–8.

The halide may also be nucleophically displaced with a three- to eight-membered heterocyclic ring, as taught for Formulae I, above. Typically, an acid addition salt form of the heterocyclic ring compound is reacted with the halogenated substrate and heated to form a homogeneous melt. Following extraction and purification, the resultant compound can be converted to an acid addition salt, such as the hydrochloride or hydrobromide, and then recrystallized.

Finally, compounds of Formula I wherein X is —$NR^1R^2$ and $R^1$ and/or $R^2$ are $C_1$–$C_4$ acyl can be prepared from the corresponding free amine by known acylation methodology using a $C_2$–$C_6$ acyl halide or anhydride.

Thus, in general, nucleophilic displacement of the 2-halo substituent in Formulae I may be effected through the use of a variety of mono-substituted and di-substituted amine salts to provide compounds of Formulae I wherein X is —$NR^1R^2$. The only functional limitation is that said amine salts must have melting points in the range of from about 170° C. to about 250° C.

Compounds of Formulae I wherein X is $C_1$–$C_4$ alkyl can be prepared by Pd(O) mediated alkyl transfer from an organostanane of the formula X-Sn-(butyl)$_3$, wherein X is the desired $C_1$–$C_4$ alkyl, to a compound of Formulae I wherein X is bromo or chloro. The reaction is generally carried out in polar aprotic solvents, such as dioxane, and at temperatures sufficient to drive the reaction to completion, for example, temperatures between 70°–100° C.

Compounds of Formulae I in which X is H may be prepared by reacting Compound C with a dehydrating and brominating agent such as phosphorous tribromide. Other agents which may be used in lieu of PBr$_3$, include agents such as SOBr$_3$, POBr$_3$, and the like. The resulting product, trans-2-bromo-6-(substituted)-5,5a,6,7,8,9-,9a,10-octahydropyrido[2,3-g]quinoline, is then reacted with tributyl tinhydride, in the presence of AIBN or another radical initiator, to provide a trans-6-(substituted)-5,5a,6,7,8,9,9a,10-octahydropyrido[2,3-g]quinoline, preferably isolated and crystallized as the dihydrochloride salt.

As can be seen above, the R group in Compounds A through D carries through the synthetic procedure intact. Thus, if it is desired to replace one alkyl group with another, or with allyl, indirect synthetic routes must be employed. Conversion of R groups is most conveniently carried out employing as substrate Compound A. For example, if R in Compound A is $C_1$–$C_4$ alkyl, reaction with cyanogen bromide yields a compound, wherein R becomes cyano. Hydrolysis of the cyano group yields the corresponding secondary amine where R is H. Similarly, reaction of Compound A, where R is methyl, with ethyl chloroformate, yields an intermediate wherein R becomes $C_2H_5$—O—CO—, which can also be hydrolyzed to yield the corresponding Compound A wherein R is H.

The secondary amine of Compound A, where R is H, can then be alkylated on the ring nitrogen with a different alkyl group, or can be allylated if an allyl group on the ring nitrogen is desired. If an allyl group is desired, the extremely reactive allyl halides can be used to ultimately yield Compound A wherein R is allyl.

The following Examples are set forth to further illustrate the invention but are in no manner to be construed as limiting the scope thereof. The following abbreviations are used: IR=infrared spectrum, NMR=nuclear magnetic resonance, MS=mass spectrogram, ME denotes the mass ion, and UV=ultraviolet.

EXAMPLE 1

(±)-trans-2-Oxo-6-propyl-1,2,3,4,5,5a,6,7,8,9,9a,10-dodecahydropyrido[2,3-g]quinoline A mixture of (±)-trans-1-propyl-6-oxo-decahydroquinolone (30.0 g, 154 mMol), acrylamide (32.8 g, 462 mMol), p-toluenesulfonic acid monohydrate (35.2 g, 185 mMol), and p-methoxyphenol (500 mg) in toluene (1000 mL) was heated to reflux, water being collected in a Dean-Stark trap. After 17 hr of reflux, the reaction was poured into dilute NaOH solution and extracted with methylene chloride The extract was dried ($Na_2SO_4$) and concentrated to give the crude product as a brown foam. Recrystallization (ethyl acetate/hexanes) provided the desired product as a tan solid (14.0 g, 37% yield). Purification of the mother liquors by flash chromatography (2:1 THF: hexanes, 0.5% $NH_4OH$) provided additional product ($R_f$=0.40, 2.6 g, 7% yield). Recrystallization of this material (ethyl acetate) provided analytically pure material. m.p.=183.0°–184.0°.

NMR (90 MHz, $CDCl_3$): 7.08 (singlet, 1H), 2.97 (doublet, J=11 Hz, 1H), 2.73–2.57 (multiplet, 1H), 2.49 (triplet, J=7 Hz, 2H), 2.45–1.37 (multiplet, 15H), 1.12–0.95 (multiplet, 1H), 0.86 (triplet, J=7 Hz, 3H).

UV (EtOH): 254 (5600).

MS (EI): 248 (5), 219 (10), 125 (100), 96 (95).

IR ($CHCl_3$): 3420, 1672 $cm^{-1}$.

Analysis for $C_{15}H_2N_2O$ Calc.: C, 72.54; H, 9.74; N, 11.28; Found: C, 72.64; H, 9.52; N, 11.29.

EXAMPLE 2

(±)-trans-2-Oxo-6-propyl-1,2,5,5a,6,7,8,9,9a,10-decahydropyrido2,3-g]quinoline hydrochloride A solution of (±)-trans-2-oxo-6-propyl-1,2,3,4,5,5a,6,7,8,9,9a,10-dodecahydropyrido[2,3-g]quinoline (12.4 g, 50 mMol) in concentrated sulfuric acid (150 mL) was heated to 100° C. for 3.5 hours. The reaction was allowed to cool, poured over ice, made basic with concentrated $NH_4OH$, and extracted sequentially with methylene chloride and 1:3 isopropanol:chloroform. The combined extracts were dried ($Na_2SO_4$) and concentrated to give the crude product as a red solid. Recrystallization (methanol/acetone) gave the desired product as a yellow solid (m.p.>270°, 3.46 g, 28% yield). A second crop provided additional material (1.22 g, 10% yield). Purification of the mother liquors by flash chromatography (10% methanol in methylene chloride, 0.5% $NH_4OH$) provided additional product ($R_f$=0.33, 1.25 g, 10% yield).

NMR (90 MHz, $CDCl_3$): 12.90 (singlet, 1H), 7.23 (doublet, J=9 Hz, 1H), 6.40 (doublet, J=9 Hz, 1H), 2.98 (doublet, J=10, 1H), 2.90 (double doublet, J=5, 16 Hz, 1H), 2.80–2.61 (multiplet, 2H), 2.49–2.10 (multiplet, 5H), 1.92 (broad doublet, J=12 Hz, 1H), 1.78–1.41 (multiplet, 5H), 1.18–1.00 (multiplet, 1H), 0.90 (triplet, J=7 Hz, 3H).

IR ($CHCl_3$): 3120, 1659, 1628, 1557 $cm^{-1}$.

UV (EtOH): 229 (8450), 313 (8100).

MS (EI): 246 (30), 217 (60), 125 (85), 124 (45), 96 (100).

One equivalent of 1N HCl solution was added to a methanolic solution of the free base. Evaporation of the volatiles followed by recrystallization (methanol/ethyl acetate) provided the monohydrochloride salt as a white solid. m.p.>270° C.

EXAMPLE 3

(±)-trans-2-Chloro-6-propyl-5,5a,6,7,8,9,9a,10-octahydropyrido[2,3-g quinoline hydrochloride Phosphorus oxychloride (272 g, 165 mL, 175 mol) was added over 6 hours to a solution of (±)-trans-2-oxo-6-propyl-1,2,5,5a,6,7,8,9,9a,10-dicahydropyrido[2,3-g]quinoline (5.75 g, 23.4 mMol) in dimethylformamide (250 mL) at 135° C. The reaction was stirred at 135° C. for 17 hours, poured over ice, and made basic with $NH_4OH$ and extracted with methylene chloride. The extract was dried ($Na_2SO_4$) and concentrated to give the crude product as a brown oil. Purification by flash chromatography (5% methanol in methylene chloride, 0.5% $NH_4OH$) gave the desired product as a brown oil (5.6 g, 90% yield).

NMR (90 MHz, $CDCl_3$): 7.76 (doublet, J=8 Hz, 1H), 7.09 (doublet, J=8 Hz, 1H), 3.12–2.90 (multiplet, 3H), 2.81–2.37 (multiplet, 4H), 2.32–2.12 (multiplet, 2H), 1.92 (broad doublet, J=12 Hz, 1H), 1.83–1.44 (multiplet, 5H), 1.11–1.05 (multiplet, 1H), 0.91 (triplet, J=7 Hz, 3H).

IR ($CHCl_3$): 1675, 1577 $cm^{-1}$.

UV (EtOH): 215 (8500), 275 (5900).

MS (EI): 266 (20), 264 (65), 237 (35), 235 (100), 138 (20), 124 (90), 96 (70).

The above oil was dissolved in methanol and a slight excess of hydrochloric acid added. Treatment of the resulting solution with decolorizing carbon and recrystallization (methanol/ethyl acetate) gave a brown solid. m.p.>250° C.

Analysis for $C_{15}H_{21}N_2Cl\cdot HCl$ Calc.: C, 59.80; H, 7.36; N, 9.30; Found: C, 60.11; H, 7.17; N, 9.00.

EXAMPLE 4

(±)-trans-2-Bromo-6-propyl-5,5a,6,7,8,9,9a,10-octahydropyrido[2,3-g]quinoline dihydrobromide Phosphorus tribromide (30.7 mL, 87.5 g, 324 mMol) was added dropwise over 22 hours to a solution of (±)-trans-2-oxo-6-propyl-1,2,5,5a,6,7,8,9,9a,10-decahydropyrido[2,3-g]quinoline (1.50 g, 6.06 mMol) in dimethylformamide (100 mL) at 100° C. The reaction was quenched by the dropwise addition of water (50 mL). This mixture was poured over ice and made basic by addition of $NH_4OH$ and extracted with methylene chloride. The extract was dried ($Na_2SO_4$) and concentrated to give a brown oil. Purification by flash chromatography (7% methanol in methylene chloride, 0.5% $NH_4OH$) gave the desired product as an orange oil ($R_f$=0.54, 1.22 g, 65% yield).

NMR (90 MHz, CDCl$_3$): 7.18 (singlet, 2H), 3.26–2.04 (multiplet, 9H), 2.01–1.02 (multiplet, 7H), 0.90 (triplet, J=7 Hz, 3H).

MS (EI): 310 (20), 308 (20), 281 (70), 279 (68), 138 (15), 125 (20), 124 (100), 96 (50).

This material was converted to the dihydrobromide salt in a manner analogous to that set forth in Example 3. Recrystallization (methanol/ethyl acetate) provided the product as a grey powder. (m.p.>275° C.).

Analysis for C$_{15}$H$_{21}$N$_2$Br.2HBr Calc.: C, 38.25; H, 4.92; N, 5.95; Found: C, 38.12; H, 4.95; N, 6.16.

EXAMPLE 5

(±)-trans-6-Propyl-5,5a,6,7,8,9,9a,10-octahydropyrido[2,3-g]quinoline dihydrochloride AIBN (25 mg) was added to a solution of (±)-trans-2-bromo-6-propyl-5,5a,6,7,8,9,9a,10-octahydropyrido[2,3-g]quinoline (570 mg, 1.85 mMol) and tributyltin hydride (1.94 g, 6.67 mMol, 3.6 eq) in toluene (25 mL) and the solution heated to 80° C. for 42 hours. The reaction was poured into a dilute HCl solution and washed with methylene chloride. The aqueous layer was made basic with NaOH solution and extracted with methylene chloride. The extract was dried (Na$_2$SO$_4$) and concentrated to give a yellow oil. Purification by flash chromatography (6% methanol in methylene chloride, NH$_4$OH) gave the desired material as a yellow oil (Rf=0.37, 368 mg, 86% yield).

NMR (90 MHz, CDCl$_3$): 8.23 (doublet, J=4 Hz, 1H), 7.25 (doublet, J=7 Hz, 1H), 6.93 (double doublet, J=4, 7 Hz, 1H), 3.28–2.08 (multiplet, 9H), 2.04–1.05 (multiplet, 7H), 0.90 (triplet, J=7 Hz, 3H).

MS (EI): 230 (50), 202 (20), 201 (100), 138 (30) 130 (40), 124 (100), 97 (70).

This material was converted to the dihydrochloride salt in a manner analogous to that set forth in Example 3. Recrystallization (methanol/ethyl acetate) provided the product as a cakey, white solid. m.p.>250° C.

Analysis for C$_{15}$H$_{22}$N$_2$.2HCl Calc.: C, 5g 41; H, 7.98; N, 9.24; Found: C, 59.23; H, 8.09; N, 9.12.

EXAMPLE 6

(±)-trans-2-Amino-6-propyl-5,5a,6,7,8,9,9a,10-octahydropyrido[2,3-g]quinoline hydrochloride and (±)-trans-2-benzylamino-6-propyl-5,5a,6,7,8,9,9a,10-octahydropyrido[2,3-g]quinoline hydrochloride A mixture of (±)-trans-2-chloro-6-propyl-5,5a,6,7,8,9,9a,10-octahydropyrido[2,3-g]quinoline hydrochloride (2.27 g, 7.50 mmol) and benzylamine hydrobromide (15.0 g) was heated to 240° C. to form a brown, molten semi-solid. After 15 minutes, the molten semi-solid was poured into water, made basic with dilute NaOH solution, and extracted with methylene chloride. The extract was dried (Na$_2$SO$_4$) and concentrated to give a brown oil. Purification by flash chromatography (6% methanol in methylene chloride, NH$_4$OH) provided (±)-trans-2-benzylamino-6-propyl-5,5a,6,7,8,9,9a,10-octahydropyrido[2,3-g]quinoline (Rf=0.35, 561 mg, 22% yield) as a brown oil.

NMR (90 MHz, CDCl$_2$): 7.32–6.80 (multiplet, 6H), 6.06 (doublet, J=9 Hz, 1H), 5.92–5.63 (multiplet, 1H), 5.33 (doublet, J=6 Hz, 2H), 3.80–1.00 (multiplet, 16H), 0.88 (triplet, J=7 Hz, 3H).

MS (EI): 335 (20), 306 (10), 224 (10), 178 (15), 125 (55), 124 (100), 96 (75), 91 (65).

This material was converted to the monohydrochloride salt in a manner analogous to that described in Example 3. Recrystallization (methanol/ethyl acetate) gave the desired monohydrochloride as an off white solid. m.p.=209.0°–210.5° C.

Analysis for C$_{22}$H$_{29}$N$_3$.HCl Calc.: C, 71.09; H, 8.13; N, 11.30; Found: C, 71.22; H, 8.22; N, 11.12.

Continued elution of the flash column provided (±)-trans-2-amino-6-propyl-5,5a,6,7,8,9,9a,10-octahydropyrido[2,3-g]quinoline (Rf=0.23, 1.02 g, 55% yield) as a brown solid.

NMR (90 MHz, CDCl$_3$): 7.20 (singlet, 2H), 7.03 (doublet, J=8 Hz, 1H), 6.18 (doublet, J=8 Hz, 1H), 3.11–0.98 (multiplet, 16H), 0.88 (triplet, J=7 Hz, 3H).

MS (EI): 245 (65), 216 (70), 138 (20), 125 (45), 124 (100), 96 (70).

This material was converted to the monohydrochloride salt in a manner analogous to that described in Example 3. Recrystallization (methanol/ethyl acetate) gave the desired monohydrochloride as tan crystals. m.p.>250° C.

Analysis for C$_{15}$H$_{23}$N$_3$.HCl Calc.: C, 63.93; H, 8.58; N, 14.91; Found: C, 64.10; H, 8.81; N, 15.01.

EXAMPLE 7

(±)-trans-2-Methylamino-6-propyl-5,5a,6,7,8,9,9a,10-octahydropyrido[2,3-g]quinoline dihydrochloride A mixture of (±)-trans-2-chloro-6-propyl-5,5a,6,7,8,9,9a,10-octahydropyrido[2,3-g]quinoline hydrochloride (1.00 g, 3.32 mmol) and methylamine hydrochloride (10 g) was heated to 240° C. to form a homogeneous molten semi-solid. After 30 minutes the molten semi-solid was poured into water, made basic with dilute NaOH solution, and extracted with methylene chloride. The extract was dried (Na$_2$SO$_4$) and concentrated to give the crude product as a brown solid. Purification by flash chromatography (10% methanol in methylene chloride, NH$_4$OH) provided (±)-trans-2-methylamino-6-propyl-5,5a,6,7,8,9, 9a,10-octahydropyrido[2,3-g]quinoline (Rf=0.44, 493 mg 57% yield) as an orange solid. This material was converted to the dihydrochloride salt in a manner analogous to that set forth in Example 3. Recrystallization (methanol/ethyl acetate) gave the desired dihydrochloride as a tan solid. m.p.>250° C.

NMR (90 MHz, CDCl$_3$): 7.08 (doublet, J=8 Hz, 1H), 6.13 (doublet, J=8 Hz, 1H), 5.60–5.24 (multiplet, 1H), 3.13–1.00 (multiplet, 19H), 0.90 (triplet, J=7 Hz, 3H).

ME (EI): 259 (100), 230 (75), 216 (20), 138 (30), 125 (60), 124 (100), 96 (75).

Analysis for C$_{16}$H$_{25}$N$_3$.HCl Calc.: C, 57.B3; H, 8.19; N, 12.64; Found: C, 57.95; H, 7.96; N, 12.60.

EXAMPLE 8

(±)-trans-2-Dimethylamino-6-propyl-5,5a,6,7,8,9,9a,10-octahydropyrido[2,3-gquinoline hydrochloride A mixture of (±)-trans-2-chloro-6-propyl-5,5a,6,7,8,9,9a,10-octahydropyrido[2,3-g]quinoline hydrochloride (1.00 g, 3.32 mmol) and dimethylamine hydrochloride (15 g) was heated to 200° C. to form a homogeneous molten semi-solid. After 30 minutes, the molten semi-solid was poured into water, made basic with dilute NaOH solution, and extracted with methylene chloride. The extract was dried (Na$_2$SO$_4$) and concentrated to give the crude product as a brown solid. Purification by flash chromatography (10% methanol in methylene chloride, NH$_4$OH) provided (±)-trans-2-dimethylamino-6-propyl-5,5a,6,7,8, 9,9a,10-octahydropyrido[2,3-g]quinoline (Rf=0.54, 568 mg, 63% yield) as an orange oil.

NMR (90 MHz, CDCl$_3$): 7.07 (doublet, J=8 Hz, 1H), 6.24 (doublet, J=8 Hz, 1H), 3.00 (singlet, 6H), 3.12–1.00 (multiplet, 16H), 0.88 (triplet, J=7 Hz, 3H). ME (EI): 273 (60), 244 (20), 230 (15), 138 (20), 125 (40), 124 (100), 96 (75).

This material was converted to the monohydrochloride salt in a manner analogous to that set forth in Example 3. Recrystallization (methanol/ethyl acetate) gave the desired monohydrochloride as off-white crystals. m.p. >260° C.

Analysis for C$_{17}$H$_{27}$N$_3$.HCl Calc.: C, 65.89; H, 9.11; N, 13.56; Found: C, 66.14; H, 9.33; N, 13.54.

EXAMPLE 9

(±)-trans-2-Pyrrolidino-6-propyl-5,5a,6,7,8,9,9a,10-octahydropyrido[2,3-g]quinoline hydrochloride A mixture of (±)-trans-2-chloro-6-propyl-5,5a,6,7,8,9,9a,10-octahydropyrido[2,3-g]quinoline hydrochloride (2.50 g, 8.3 mmol) and pyrrolidine hydrochloride (10 g) was heated to 210° C. to form a homogeneous molten semi-solid. After 45 minutes the molten semi-solid was poured into water, made basic with dilute NaOH solution, and extracted with methylene chloride The extract was dried (Na$_2$SO$_4$) and concentrated to give the crude product as a brown solid. Purification by flash chromatography (10% methanol in methylene chloride, NH$_4$OH) provided (±)-trans-2-pyrrolidino-6-propyl-5,5a,6,7,8,9,9a,10-octahydropyrido[2,3-g]quinoline (Rf=0.45, 1% 32 g, 53% yield) as a brown oil.

NMR (90 MHz, CDCl$_2$): 7.03 (doublet, J=8 Hz, 1H), 6.07 (doublet, J=8 Hz, 1H), 3.55–3.11 (multiplet, 4H), 3.11–1.00 (multiplet, 20H), 0.89 (triplet, J=7 Hz, 3H).

ME (EI): 299 (95), 270 (35), 256 (30), 173 (55), 138 (25), 125 (50), 124 (100), 96 (80).

This material was converted to the monohydrochloride salt in a manner analogous to that set forth in Example 3. Recrystallization (methanol/ethyl acetate) gave the desired monohydrochloride as a tan solid. m.p.=238.0°–240.0° C. (dec.).

Analysis for C$_{19}$H$_{29}$N$_3$.HCl Calc.: C, 67.93; H, 9.00; N, 12.51; Found: C, 67.67; H, 8.94; N, 12.28

The compounds of this invention are dopamine agonists and, like other dopamine agonists, are effective in lowering serum prolactin levels in rats according to the following procedure.

Adult male rats of the Sprague-Dawley strain weighing about 200 g were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test drug in order to keep prolactin levels uniformly elevated. The test compounds were dissolved in 10 percent ethanol and injected intraperitoneally. Each compound was administered at each dose level to a group of 10 rats, and a control group of 10 intact males received an equivalent amount of 10 percent ethanol. One hour after treatment, all rats were killed by decapitation, and 150 μl aliquots of serum were assayed for prolactin.

The difference between the prolactin level of the treated rats and prolactin level of the control rats, divided by the prolactin level of the control rats gives a number that, when multiplied by 100, is the percent inhibition of prolactin secretion attributable to the compounds of this invention. These inhibition percentages are given in Table 1.

TABLE I

Serum Prolactin Inhibition*

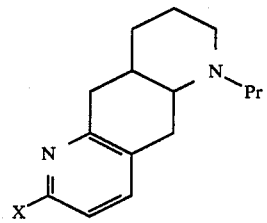

| X | Salt | Dose (μg/kg, ip) | Prolactin control (ng/ml) | Prolactin treatment (ng/ml) | Percent inhibition | Significance level |
|---|---|---|---|---|---|---|
| H | 2 HCl | 1 | 33.19 ± 2.91 | 28.28 ± 2.83 | 15 | 0.24 (NS) |
|  |  | 5 | 33.19 ± 2.91 | 29.96 ± 3.11 | 10 | 0.46 (NS) |
|  |  | 10 | 33.19 ± 2.91 | 19.30 ± 1.31 | 42 | <0.001 |
|  |  | 50 | 47.08 ± 4.66 | 5.48 ± 0.42 | 88 | <0.0001 |
| OH | HCl | 1000 | 47.08 ± 4.66 | 32.7 ± 3.30 | 31 | 0.023 |
| Cl | HCl | 50 | 78.8 ± 7.1 | 42.2 ± 1.9 | 46 | <0.001 |
| Br | 2 HBr | 50 | 37.99 ± 4.06 | 41.8 ± 3.14 | (10) | <0.5 (NS) |
|  |  | 1000 | 47.1 ± 4.66 | 11.39 ± 2.12 | 76 | <0.0001 |
| NH$_2$ | HCl | 1 | 47.1 ± 4.66 | 26.77 ± 2.43 | 43 | 0.02 |
|  |  | 5 | 47.1 ± 4.66 | 15.50 ± 1.15 | 67 | <0.0001 |
|  |  | 10 | 47.1 ± 4.66 | 14.04 ± 2.17 | 70 | <0.0001 |
|  |  | 50 | 37.99 ± 4.06 | 5.86 ± 0.39 | 84 | <0.001 |
| NHMe | 2 HCl | 1 | 47.1 ± 4.66 | 34.6 ± 3.58 | 26 | 0.049 |
|  |  | 5 | 47.1 ± 4.66 | 23.60 ± 2.88 | 50 | 0.0008 |
|  |  | 10 | 47.1 ± 4.66 | 19.61 ± 3.09 | 58 | <0.0001 |
|  |  | 50 | 37.99 ± 4.06 | 9.36 ± 1.09 | 75 | <0.001 |
| NHCH$_2$Ph | HCl | 1 | 47.1 ± 4.66 | 34.3 ± 3.44 | 27 | 0.042 |
|  |  | 5 | 47.1 ± 4.66 | 22.8 ± 3.33 | 52 | 0.0007 |
|  |  | 10 | 47.1 ± 4.66 | 19.68 ± 2.15 | 58 | 0.0001 |
|  |  | 50 | 37.99 ± 4.06 | 9.23 ± 0.74 | 76 | <0.001 |
| N(CH$_2$)$_4$ | HCl | 50 | 37.99 ± 4.06 | 16.76 ± 1.64 | 56 | <0.001 |
| NMe$_2$ | HCl | 1 | 47.1 ± 4.66 | 23.79 ± 3.05 | 49 | 0.0008 |

TABLE I-continued
Serum Prolactin Inhibition*

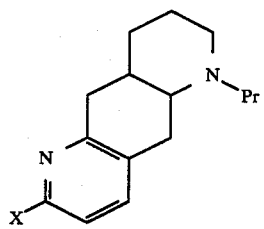

| X | Salt | Dose (μg/kg, ip) | Prolactin control (ng/ml) | Prolactin treatment (ng/ml) | Percent inhibition | Significance level |
|---|------|------------------|---------------------------|-----------------------------|--------------------|--------------------|
|   |      | 5                | 47.1 ± 4.66               | 14.86 ± 1.63                | 68                 | <0.0001            |
|   |      | 10               | 47.1 ± 4.66               | 12.22 ± 1.23                | 74                 | <0.0001            |
|   |      | 50               | 37.99 ± 4.06              | 8.97 ± 1.26                 | 76                 | <0.001             |

*All compounds were treated as a racemic mixture.

As Table I demonstrates, the compounds of this invention are dopamine agonists and are therefore effective for the treatment of a variety of disorders including Parkinsonism, anxiety, depression, hypertension, glaucoma, sexual dysfunction, and prolactin mediated disorders such as gallactorrhea, amenorrhea, prolactinomas and the inhibition of postpartum lactation.

In using the compounds of this invention to inhibit prolactin secretion, treat Parkinson's syndrome, or treat any other disorder noted above, a compound according to Formulae I, or a pharmaceutically acceptable salt thereof, is administered to a mammalian subject suffering from elevated prolactin levels, Parkinsonism, or any other disorder noted above, in an amount effective to reduce prolactin, treat Parkinsonism, or treat any other of the above disorders. The compounds may be administered either orally or parenterally. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, a compound of the invention, either as the free base or in the form of a salt thereof, can also be mixed with standard pharmaceutical carriers, diluents or excipients, and loaded into empty telescoping gelatin capsules or pressed into tablets. The oral dosage range is from about 0.01 to about 10 mg/kg of subject matter weight, while the parenteral dosage range is from about 0.0025 to 2.5 mg/kg of subject matter weight.

The compounds of this invention may be administered for therapeutic purposes in a variety of pharmaceutical formulations as illustrated below. In the formulations below, the term "Active compound" refers to any compound of the present invention. Preferred compounds which may be used as Active compounds in the formulations below are these compounds disclosed in Examples 2-9, above.

Hard gelatin capsules are prepared using the following ingredients:

|                | Quantity (mg./capsule) |
|----------------|------------------------|
| Active compound | 0.01-20               |
| Starch dried   | 200                    |
| Magnesium stearate | 10                 |

The above ingredients are mixed and filled into hard gelatin capsules.

A tablet formulation is prepared using the ingredients below:

|                           | Quantity (mg./tablet) |
|---------------------------|-----------------------|
| Active compound           | 0.01-20               |
| Cellulose, microcrystalline | 400                 |
| Silicon dioxide, fumed    | 10                    |
| Stearic acid              | 5                     |

The components are blended and compressed to form tablets.

A tablet formulation is also prepared using the ingredients

|                                           | Quantity (mg./tablet) |
|-------------------------------------------|-----------------------|
| Active ingredient                         | 0.01-20               |
| Starch                                    | 45                    |
| Microcrystalline cellulose                | 35                    |
| Polyvinylpyrrolidone (as 10% solution in water) | 4               |
| Sodium carboxymethyl starch               | 4.5                   |
| Magnesium stearate                        | 0.5                   |
| Talc                                      | 1                     |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets.

Capsules are also prepared as follows:

|                            | Quantity (mg./capsule) |
|----------------------------|------------------------|
| Active ingredient          | 0.01-20                |
| Starch                     | 59                     |
| Microcrystalline cellulose | 59                     |

| | Quantity (mg./capsule) |
|---|---|
| Magnesium stearate | 2 |

The active ingredient, cellulose, starch and magnesium stearate are blended, passed through a No. 45 mesh U.S. sieve, and filled into hard gelatin capsules.

Suspensions each containing 0.01-20 mg. of medicament per 5 ml. dose can be made as follows:

| | |
|---|---|
| Active ingredient | 0.01-20 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

I claim:

1. A compound of the formulae

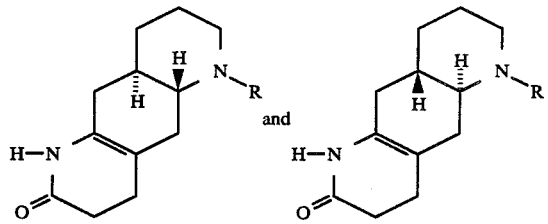

wherein:

R is $C_1$-$C_4$ alkyl, allyl or cyclopropylmethyl; and acid addition salts thereof.

* * * * *